(12) United States Patent
Heden et al.

(10) Patent No.: US 9,519,291 B2
(45) Date of Patent: Dec. 13, 2016

(54) COORDINATION OF SOLVENT DELIVERY WITH PRE-INJECTION OPERATIONS IN A LIQUID CHROMATOGRAPH

(75) Inventors: John Heden, Hollis, NH (US); John Lamoureux, Franklin, MA (US); Miguel Soares, Norton, MA (US); Guo-Zhong Li, Westborough, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 1135 days.

(21) Appl. No.: 13/511,667

(22) PCT Filed: Nov. 11, 2010

(86) PCT No.: PCT/US2010/056318
§ 371 (c)(1),
(2), (4) Date: Aug. 22, 2012

(87) PCT Pub. No.: WO2011/066110
PCT Pub. Date: Jun. 3, 2011

(65) Prior Publication Data
US 2012/0304745 A1    Dec. 6, 2012

Related U.S. Application Data

(60) Provisional application No. 61/264,488, filed on Nov. 25, 2009, provisional application No. 61/297,911, filed on Jan. 25, 2010.

(51) Int. Cl.
*G01N 30/24* (2006.01)
*G05D 7/06* (2006.01)

(52) U.S. Cl.
CPC ............ *G05D 7/0676* (2013.01); *G01N 30/24* (2013.01)

(58) Field of Classification Search
CPC ........................................................ G01N 30/24
USPC ................ 73/61.55, 863.01, 864.81–864.87; 137/625.15, 625.46; 251/160
See application file for complete search history.

(56) References Cited

U.S. PATENT DOCUMENTS

| 5,814,742 | A | 9/1998 | Vissers et al. | |
| 7,178,386 | B1 * | 2/2007 | Gamble ............... | G01N 30/466 210/198.2 |
| 8,196,456 | B2 * | 6/2012 | Hochgraeber ......... | G01N 30/20 73/61.55 |

(Continued)

OTHER PUBLICATIONS

International Search Report in counterpart PCT Application No. PCT/US2010/056318, mailed on Jan. 21, 2011; 2 pages.

*Primary Examiner* — Hezron E Williams
*Assistant Examiner* — Hoang Nguyen
(74) *Attorney, Agent, or Firm* — Schmeiser, Olsen & Watts LLP

(57) ABSTRACT

A liquid chromatography system includes an autosampler that prepares a sample for introduction to a solvent stream and a solvent delivery system that delivers a solvent stream to the autosampler. Delivery of the solvent stream occurs in parallel with the autosampler's pre-injection operations. The autosampler starts pre-injection operations to make the sample ready for injection into the mixture stream, and the solvent delivery system starts delivery of a solvent stream to the autosampler. The start of the solvent stream delivery is coordinated with the start of the pre-injection operations such that the solvent stream arrives at the autosampler approximately coincident with when the autosampler completes the pre-injection operations, making the sample ready for injection.

15 Claims, 3 Drawing Sheets

(56) References Cited

U.S. PATENT DOCUMENTS

| | | |
|---|---|---|
| 8,794,052 B2* | 8/2014 | Maeda .................. G01N 30/20 73/61.55 |
| 2002/0010566 A1 | 1/2002 | Chester et al. |
| 2004/0226884 A1* | 11/2004 | O'Connor ............. B01L 3/5025 210/634 |
| 2006/0193748 A1* | 8/2006 | Tai ......................... G01N 30/34 422/70 |
| 2007/0000312 A1 | 1/2007 | Weissgerber |
| 2007/0117212 A1* | 5/2007 | Kautz ............... B01L 3/502784 436/137 |
| 2008/0206067 A1 | 8/2008 | De Corral et al. |
| 2009/0062966 A1* | 3/2009 | Pensak, Jr. ......... G01N 35/1097 700/285 |
| 2009/0076631 A1 | 3/2009 | Witt et al. |
| 2009/0145205 A1 | 6/2009 | Hochgraeber et al. |
| 2009/0294363 A1 | 12/2009 | Liu |

* cited by examiner

COORDINATION OF SOLVENT DELIVERY WITH PRE-INJECTION OPERATIONS IN A LIQUID CHROMATOGRAPH

RELATED APPLICATION

This application claims the benefit of U.S. Provisional Application Ser. No. 61/264,488, filed Nov. 25, 2009, titled "Coordination of Solvent Delivery with Pre-Inject Operations in a Liquid Chromatograph," and of U.S. Provisional Application Ser. No. 61/297,911, filed Jan. 25, 2010, titled "Coordination of Solvent Delivery with Pre-injection Operations in a Liquid Chromatograph," the entireties of which provisional applications are incorporated by reference herein.

FIELD OF THE INVENTION

The invention relates generally to chromatography systems. More specifically, the invention relates to coordinating solvent delivery with pre-injection operations in a liquid chromatography system.

BACKGROUND

Chromatography is a set of techniques for separating a mixture into its constituents. For instance, in a liquid chromatography application, a pump takes in and delivers a mixture of liquid solvents to an autosampler, where a sample awaits the mixture's arrival. In an isocratic chromatography application, the composition of the liquid solvents remains unchanged, whereas in a gradient chromatography application, the solvent composition varies over time. The mobile phase, comprised of a sample dissolved in the solvent stream, passes to a column of particulate matter, referred to as the stationary phase. By passing the mixture through the column, the various components in the sample separate from each other at different rates and thus elute from the column at different times. A detector receives the elution from the column and produces an output from which the identity and quantity of the analytes may be determined.

Historically, the pump's delivery of the solvent stream to the autosampler did not start until after the autosampler completed its pre-injection operations and was ready to initiate the actual injection event (i.e., a valve transition to introduce the sample to the stream). Thus, the process was sequential: first, start and finish the autosampler's pre-injection operations and, then, start and finish the solvent stream delivery.

Before the solvent stream reaches the injector, however, and thus before injection can take place, a pre-injector dwell volume (also called the delay volume) must first be delivered. In general, the pre-injector dwell volume is the volume of liquid from the point where the solvent mixture forms to the injector valve. Depending upon various factors, such as the use of a mixer, pre-injector dwell volumes can be relatively large (in hundreds of microliters), and, therefore, introduce a sizeable delay to the start of each injection. Historically, however, this delay was insignificant compared to the lengthy chromatographic run times that took tens of minutes and even hours.

This delay becomes problematic, though, when run times are in terms of just a few minutes. For example, if the pre-injector dwell volume is approximately 400 μL, and the pump produces a flow rate of 350 μL per minute, then the time for the solvent stream to reach the injector valve is over a minute. Thus, the dead time introduced by the pre-injector dwell volume can be a significant percentage of a run, particularly when run times are only minutes in length.

SUMMARY

In one aspect, the invention features a method for introducing a sample to a solvent stream. An autosampler starts pre-injection operations to make the sample ready for injection into the mixture stream. Delivery of a solvent stream to the autosampler is started. The start of the solvent stream delivery is coordinated with the start of the pre-injection operations such that the solvent stream arrives at the autosampler approximately coincident with when the autosampler completes the sample pre-injection operations to make the sample ready for injection.

In other aspects, the invention features a liquid chromatography system and method for introducing a sample to a solvent stream. An autosampler performs pre-injection operations to make the sample ready for injection into the mixture stream. A solvent delivery system starts delivery of the solvent stream towards the autosampler before the autosampler completes the pre-injection operations and the sample is ready for injection.

In still another aspect, the invention features a method for introducing a sample into a solvent stream. A first message is sent from a solvent delivery system to an autosampler instructing the autosampler to initiate preparing a sample for injection into a mixture stream. After a specified amount of time elapses after the first message is sent to the autosampler, a second message is sent from the solvent delivery system to the autosampler to inject the sample into a mixture stream.

In still another aspect, the invention features a method for introducing a sample into a solvent stream. A first message is sent from an autosampler to a solvent delivery system instructing the solvent delivery system to assume control of a chromatographic injection sequence. In response to the message, a second message is sent from the solvent delivery system to the autosampler accepting control of the chromatographic injection sequence. In response to accepting control, the solvent delivery system coordinates a start of solvent stream delivery with a start of pre-injection operations of the autosampler.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Liquid chromatography systems operating in accordance with the principles of the invention perform delivery of a solvent stream in parallel with the pre-injection operations performed by the autosampler. As used herein, the term "solvent stream" contemplates both aforementioned types of chromatography applications: (1) unchanging (isocratic) solvent mixtures; and (2) gradient solvent mixtures. The parallel processing reduces the effect of a pump's pre-injector dwell volume on the throughput of a chromatographic run. Instead of waiting until the autosampler completes its pre-injection operations before starting delivery of the solvent stream, a solvent delivery system begins delivery before or during the autosampler's pre-injection operations.

The timing as to when to start delivery of the solvent stream is based on a comparison of calculations performed by the autosampler and the solvent delivery system. Each instrument (i.e., the autosampler and the solvent delivery system) calculates its expected time to complete its pre-injection operations: the solvent delivery system calculates the time for the dwell volume to traverse to the injector valve at a particular flow rate; and the autosampler calculates the time to complete various pre-injection operations.

Based on these calculations, the solvent delivery system identifies which of the two instruments requires more time to complete its pre-injection operations. The slower instrument starts its pre-injection operations first, and the faster instrument starts its own pre-injection operations at a determined moment thereafter. That moment occurs before the slower instrument completes its pre-injection operations, so that the pre-injection operations of the faster instrument occur in parallel with the pre-injection operations of the slower instrument. The timing of that moment is such that the solvent stream arrives at the injector valve at approximately the same time as or slightly later than (but never before) when the autosampler completes its pre-injection sequence.

Figure 1:
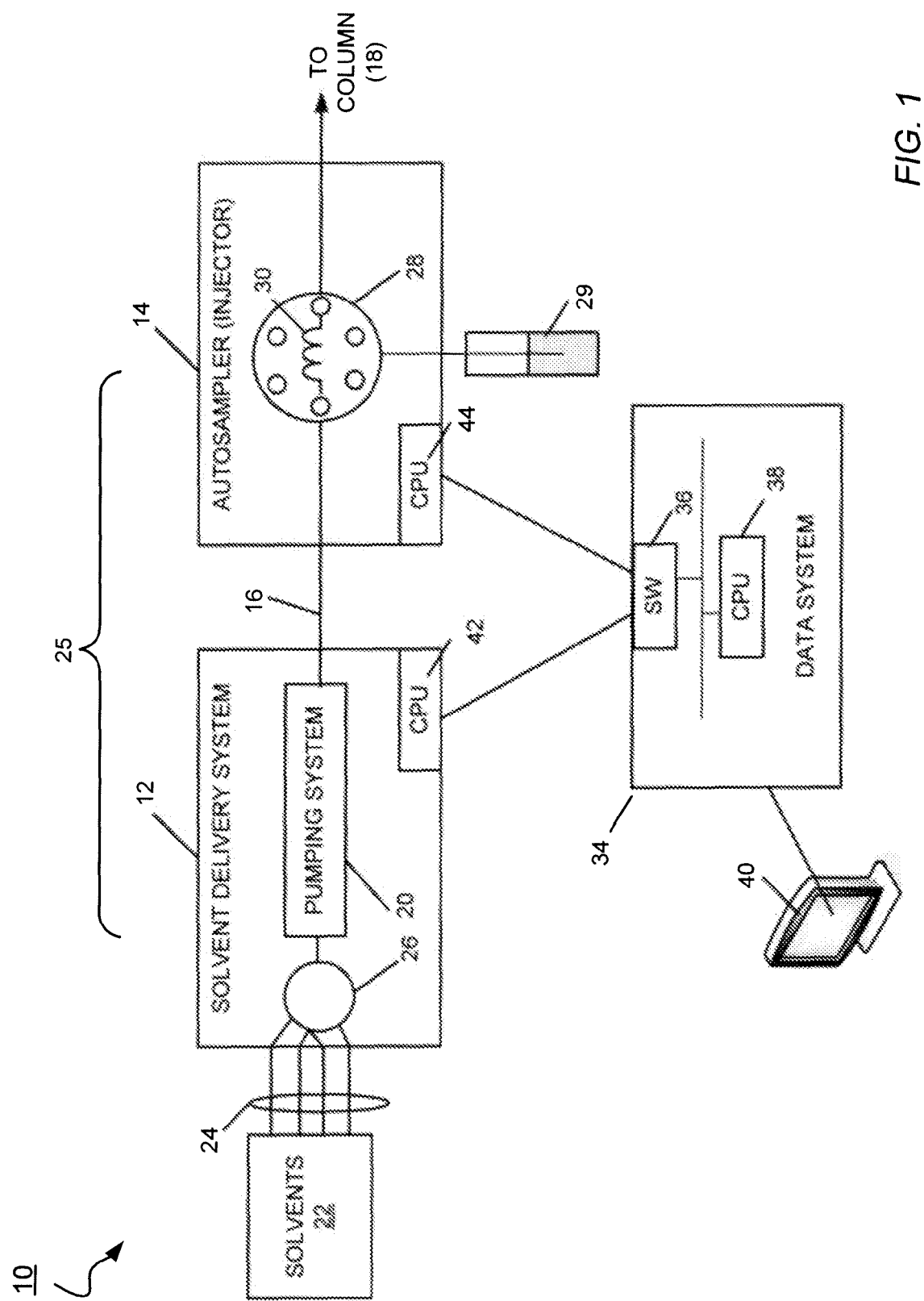
FIG. 1 is a functional block diagram of an embodiment of a liquid chromatography system.

FIG. 1 shows an embodiment of a liquid chromatography system 10 for separating a mixture into its constituents. The liquid chromatography system 10 includes a solvent delivery system 12 in fluidic communication with an autosampler 14 (also called an injector or sample manager) through tubing 16. The autosampler 14 is in fluidic communication with a chromatographic column 18 of particulate matter. A detector (not shown), for example, a mass spectrometer, is in fluidic communication with the column 18 to receive the elution. Preferred liquid chromatography systems and their various subsystems are sold under various ACQUITY™ trademarks by Waters Corporation of Milford, Mass.

The solvent delivery system 12 includes a pumping system 20 in fluidic communication with reservoirs 22 from which the pumping system 20 draws liquid solvents through tubing 24. In one embodiment, the pumping system 20 is embodied by a low-pressure mixing pumping system having a single pump with two pistons (or heads). Pumps with two pistons can come in one of two types: the pistons operate in parallel, where one piston draws solvent while the other delivers solvent to the autosampler, or in series (a primary piston and an accumulator piston), as described in U.S. patent application Ser. No. 11/631,354, the entirety of which application is incorporated by reference herein.

In a low-pressure pumping system, the mixing of solvents occurs before the pump. The solvent delivery system 12 has a mixer 26 in fluidic communication with the solvent reservoirs 22 to receive various solvents in metered proportions. This mixing of solvents occurs in accordance with an intake profile, and produces a solvent stream that remains unchanged (isocratic) or varies over time (gradient). The pumping system 20 is in fluidic communication with the mixer 26 to draw a continuous flow of a solvent mixture therefrom for delivery to the autosampler 14. To draw and deliver the solvent mixture, the pumping system 20 can provide a flow rate in the range of 0.010 ml/min to 2 ml/min at 15,000 psi.

Examples of pumping systems that can be used to implement the pumping system 20 include, but are not limited to, the ACQUITY HPLC Binary Solvent Manager, manufactured by Waters Corp. of Milford, Mass. Although described herein primarily with reference to low-pressure mixing pump systems, the principles of the invention apply also to high-pressure pumping systems. In contrast to a low-pressure pumping system, in which the mixing occurs on the intake side of the pump, the mixing of solvents in a high-pressure pumping system occurs after the solvent stream passes through the pump. Because of their respective locations for mixing solvents, high-pressure pumping systems have less dwell volume than low-pressure pumping systems.

The autosampler 14 includes an injector valve 28 having a sample loop 30. The injector valve 28 can be a multi-port, multiple-position rotary valve of a type described in U.S. patent application Ser. No. 11/658,985, the entirety of which patent application is incorporated by reference herein. The autosampler 14 operates in one of two states: a load state and an injection state. In the load state, the position of the injector valve 28 is such that the autosampler 14 loads the sample 29 into the sample loop 30; in the injection state, the position of the injector valve 28 changes so that autosampler 14 introduces the sample in the sample loop 30 into the continuously flowing mobile phase from the solvent delivery system. The mobile phase thus carries the sample into the column 18. The pre-injection dwell volume 25 of this embodiment of chromatography system 10 extends from where the solvent mixture forms within the mixer 26 on the intake side of the pumping system 20 to the injector valve 28 of the autosampler 14.

The chromatography system 10 further includes a data system 34 that is in signal communication with the solvent delivery system 12 and the autosampler 14. The data system 34 has a processor 38 and a switch 36 (e.g., an Ethernet switch) for handling signal communication between the solvent delivery system 12 and autosampler 14, as described herein. Signal communication among the various systems and instruments is electrical, using wired transmission.

A host computing system 40 is in communication with the data system 34 by which a user can download various parameters and profiles (e.g., an intake velocity profile) to the data system 34. The downloaded parameters include method parameters for the solvent delivery system 12 and the autosampler 14 and injection parameters for the autosampler 14. Method parameters for the solvent delivery system 12 include, but are not limited to, a user-settable pre-injection (dwell) volume parameter and an initial flow rate parameter. Users may add different mixers and tubing, which affect the dwell volume; the pre-injection volume parameter provides a way to specify precisely the dwell volume of their system. A typical pre-injection dwell volume is 350 µl. Downloaded injection parameters include, but are not limited to, sample vial location and sample volume.

The solvent delivery system 12 has a processor 42 for controlling the flow rate of the pumping system and the solvent stream formation in accordance with downloaded method parameters. The processor 42 also calculates an amount of time for delivering the solvent stream to the injector valve of the autosampler 14 based on the pre-injection dwell volume and flow rate.

The autosampler 14 has a processor 44 for controlling the loading and injection stages of operation in accordance with downloaded method and injection parameters. Before injection of the sample into the mobile phase can take place, the autosampler 14 has various pre-injection operations to perform. Among others, such operations include washing, purging, and aspirating the sample into the sample loop. The processor 44 calculates the amount of time for performing its pre-injection operations.

Figure 2A:
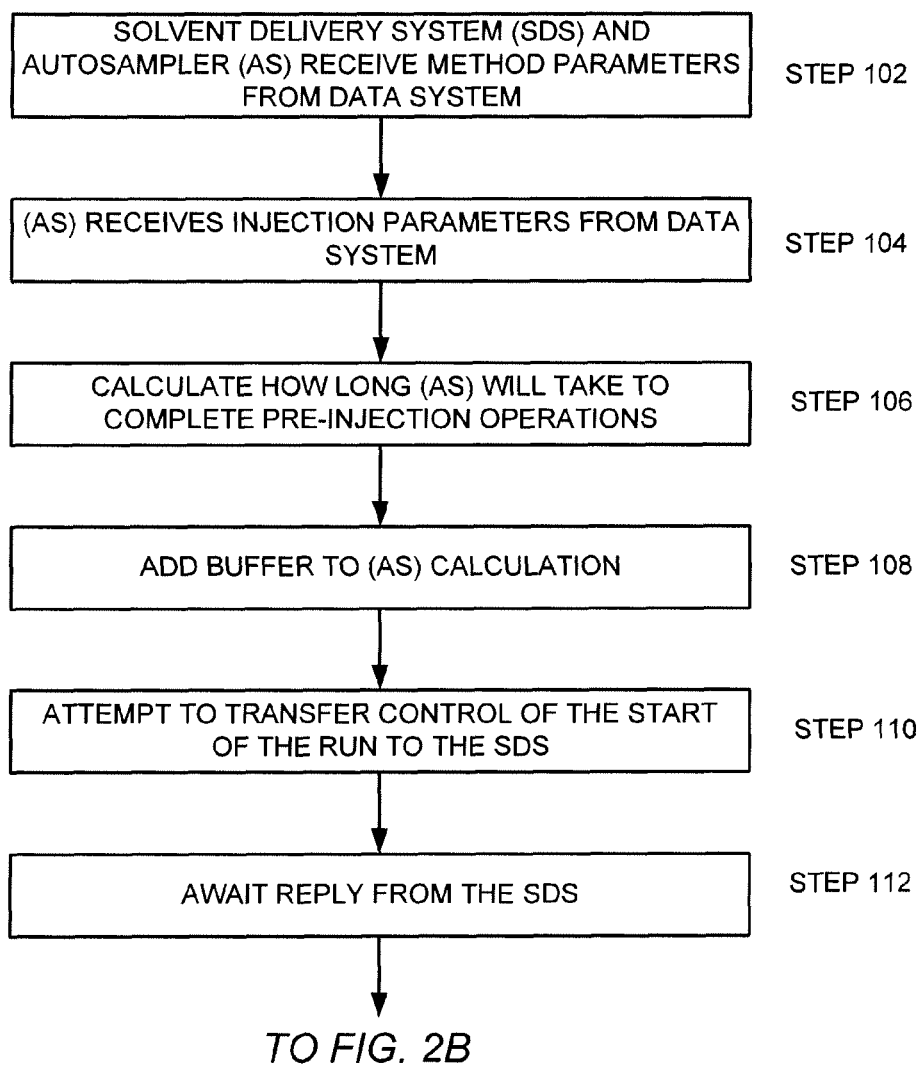
FIG. 2A and FIG. 2B are flow diagrams of an embodiment of a process for coordinating delivery of a solvent stream to the autosampler with the autosampler's execution of pre-injection operations.
Figure 2B:
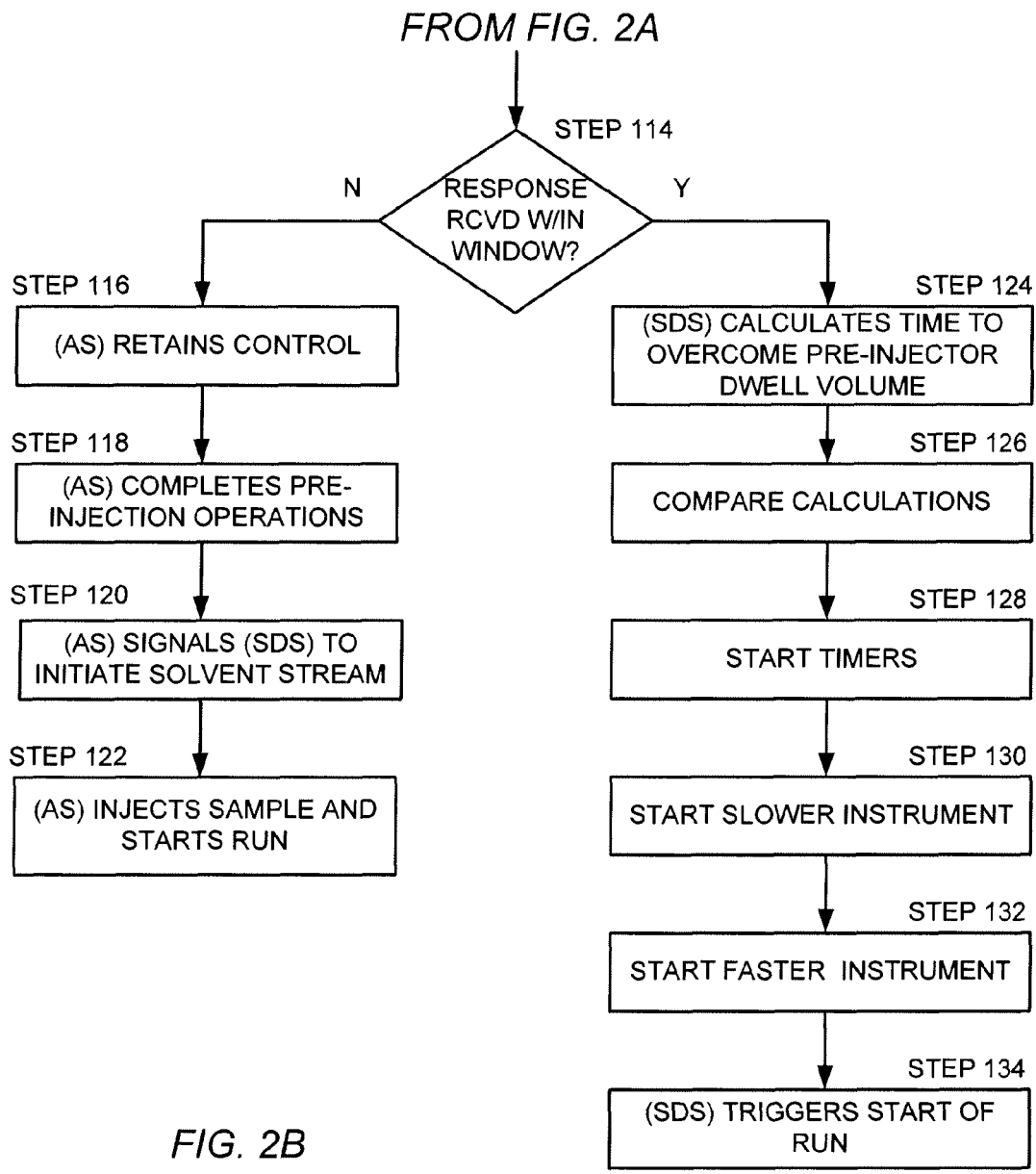

FIG. 2A and FIG. 2B show an embodiment of a process 100 for coordinating solvent delivery with the pre-injection operations of the autosampler. In the description of the process 100, reference is made also to elements shown in FIG. 1. At step 102, the solvent delivery system 12 and autosampler 14 receive their method parameters from the data system 34. The autosampler 14 also receives (step 104) its injection parameters from the data system 34. Based on an analysis of the injection parameters, the autosampler calculates (step 106) the amount of time needed to complete its pre-injection operations, for example, axes moves, sample draw, and air gap draw. A time buffer (or guard band) can be added (step 108) to the calculated time in order to ensure that the autosampler completes its pre-injection operations before the solvent stream arrives at the injector valve. In one embodiment, the time buffer is 5 seconds.

The autosampler attempts (step 110) to transfer to the solvent delivery system responsibility for starting the chromatographic injection sequence (i.e., when to start pre-injection operations of the autosampler relative to those of the solvent delivery system). In one embodiment, the autosampler sends the solvent delivery system a "delegate start run" message containing the time calculated for completing the autosampler's pre-injection operations. The autosampler then waits (step 112) a predefined maximum period (e.g., 500 ms) for the solvent delivery system to respond with a "delegate start run acknowledged" message.

If, at step 114, the autosampler does not receive a response within the defined period, the autosampler retains (step 116) control of the chromatographic injection sequence. For example, a method parameter received by the solvent delivery system may specify an initial condition of a 0 ml/min flow rate, signifying that the pumping system will not be flowing and, therefore, not delivering a solvent stream. In that event, the solvent delivery system does not send a "delegate start run acknowledged" message to the autosampler, and thus the autosampler retains responsibility for the chromatographic injection sequence. Sequential processing ensues: the autosampler starts and completes (step 118) its pre-injection operations and, then, after the sample is ready for injection, signals (step 120) the solvent delivery system to initiate the solvent stream. The autosampler then injects the sample and immediately afterwards sends (step 122) a "start run" message to all instruments in the chromatography system, including the solvent delivery system, to start the run.

Alternatively, at step 114, the solvent delivery system 12 assumes responsibility for the chromatographic injection sequence by responding to the autosampler with a "delegate start run acknowledged" message. At step 124, the solvent delivery system calculates the amount of time needed to overcome its pre-injection dwell volume and deliver the solvent stream to the injector valve 28 based on the initial flow rate and pre-injector volume method parameters. For example, consider that the solvent delivery system has a 400 µl dwell volume, and a 0.6 mL/min flow rate, the solvent delivery system calculates that it will take 40 seconds to overcome the pre-injector dwell volume and deliver the solvent stream to the injector valve.

The solvent delivery system compares (step 126) the received calculation for completing autosampler's pre-injection operations with its own calculated time for delivering the solvent stream to the injector valve. The comparison serves to identify which of the two instruments (i.e., the solvent delivery system or the autosampler) is the slower instrument and which is the faster instrument. The solvent delivery system also calculates a difference in the two calculated times (herein, called delta t or $\Delta t$). For example, if the autosampler calculation is 40 seconds, and the solvent delivery system calculation is 75 seconds, then the autosampler is the faster of the two instruments and the delta t ($\Delta t$) is 35 seconds.

At step 128, two timers start running in the solvent delivery system. One timer controls when to start the slower instrument, and is referred to herein as the slow timer; the other timer controls when to start the faster instrument, and is referred to herein as the fast timer. The slow timer is set to start the slower instrument at a specific time (e.g., immediately) and the fast timer is set to start the faster instrument at a designated time after the slower instrument begins operations. That designated time is the calculated delta t ($\Delta t$), and is designed to cause the faster instrument to complete its pre-injection operations at the same moment the slower instrument completes its pre-injection operations.

At step 130, the slow timer starts the slower instrument, and at step 132, the fast timer starts the faster instrument. To direct the autosampler to start its pre-injection operations at the appropriate time, whether the autosampler is the slower or the faster instrument, the assigned timer sends the autosampler a "continue run" message. The timer assigned to the solvent delivery system, whether it is the slower or faster instrument, starts the solvent stream at its set time.

In the event the completion time calculated by the autosampler is equal to the solvent stream delivery time calculated by the solvent delivery system, both instruments start concurrently (delta t ($\Delta t$) is equal to 0), provided the autosampler's calculation includes a built-in time buffer to ensure sample injection occurs before delivery of the solvent stream.

When the solvent delivery system completes delivery of the solvent stream to the injector valve, which is at the same time (or slightly later than) the autosampler completes its pre-injection operations, the solvent delivery system triggers (step 134) injection and the start of the chromatographic run by sending a "start run" message to all instruments in the chromatography system. This start run message signals the actual injection event, in which the injector valve transitions, the sample enters the mobile phase, and data collection begins. By the time the solvent delivery system sends the "start run" message, the autosampler has presumably completed its pre-injection operation, including loading the sample into the sample loop. In the event that the autosampler is still performing pre-injection operations at the time of receiving the start run message, for example, because of inaccurate completion estimations, the autosampler generates an error message and stops the run before the injection event can occur.

As an example of the above-described process, consider that the autosampler calculates a 45-second completion time for its pre-injection operations, and the solvent delivery system calculates a 1-minute completion time. After comparing the two calculations, the solvent delivery system determines it is the slower of the two instruments and starts itself first. Fifteen seconds after starting, the solvent delivery system signals the autosampler to start its pre-injection operations. Forty-five seconds after signaling the autosampler to start, the solvent delivery system signals the autosampler to transition the injector valve to introduce the sample to the solvent stream. The process takes 60 seconds to complete, whereas a sequential process would have taken 105 seconds to complete. Thus, the parallel process takes 60 seconds, which is approximately a 43% ((105−60)/105*100) improvement over the sequential process.

As another example, consider that the autosampler again calculates a 45-second completion time, while the solvent delivery system calculates a 40-second solvent stream delivery time. After comparing the two calculations, the solvent delivery system signals the autosampler to start, the autosampler in this example being the slower instrument. Five seconds later, the solvent delivery system initiates the solvent stream, and 40 seconds after initiating the solvent stream, the solvent delivery system triggers the injection event and the start of the run by sending a "start run" message to the autosampler. The parallel process takes 45 seconds to complete, whereas a sequential process would have taken 85 seconds to complete.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects. All such forms may be generally referred to herein as a "system." Furthermore, aspects of the present invention may take the form of a computer program product embodied in one or more computer readable storage medium(s) having computer readable program code embodied thereon.

A computer readable storage medium may be any tangible medium that can contain, or store a program for use by or in connection with an instruction execution system, apparatus, or device. A computer readable storage medium may be, for example, but not limited to, an electronic, magnetic, optical, electromagnetic, infrared, or semiconductor system, apparatus, or device, or any suitable combination of the foregoing. More specific examples of the computer readable storage medium include, but are not limited to, the following: a portable computer diskette, a hard disk, a random access memory (RAM), a read-only memory (ROM), an erasable programmable read-only memory (EEPROM, EPROM, Flash memory), an optical fiber, a portable compact disc read-only memory (CD-ROM), an optical storage device, a magnetic storage device, or any suitable combination of the foregoing.

Program code embodied on a computer readable medium may be transmitted using any appropriate medium, including but not limited to wireless, wire-line, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages.

Aspects of the present invention are described below with reference to flowchart illustrations and/or block diagrams of methods, apparatus (systems), and computer program products according to embodiments of the invention. Each block of the flowchart illustrations and/or block diagrams, and combinations of blocks in the flowchart illustrations and/or block diagrams can be implemented by computer program instructions.

Computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

Computer program instructions may also be stored in a computer readable storage medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the FIGs. illustrate the architecture, functionality, and operation of possible implementations of systems, methods, and computer program products according to various embodiments of the present invention. In this regard, each block in the flowchart or block diagrams may represent a module, segment, or portion of program code, which comprises one or more executable instructions for implementing the specified logical function(s). The functions noted in the blocks may occur out of the order noted in the FIGS. For example, two blocks shown in succession may be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the invention has been shown and described with reference to specific preferred embodiments, it should be understood by those skilled in the art that various changes in form and detail may be made therein without departing from the spirit and scope of the invention as defined by the following claims.

What is claimed is:

1. A method for introducing a sample to a solvent stream, comprising:
   calculating a first amount of time for completing pre-injection operations of an autosampler and a second amount of time for delivering the solvent stream to the autosampler;
   comparing the first amount of time and the second amount of time to identify which amount of time is greater than the other amount of time and to quantify a time difference between the amounts of time;
   starting pre-injection operations by the autosampler to make the sample ready for injection into the solvent stream; and
   starting delivery of the solvent stream to the autosampler, wherein the starting of the pre-injection operations and the starting of the delivery of the solvent stream occur at times that differ by approximately the time difference.

2. The method of claim 1, further comprising triggering an injection event at approximately the same time that the autosampler completes the pre-injection operations.

3. The method of claim 1, further comprising adding a buffer of time to the amount of time for completing the pre-injection operations.

4. The method of claim 1, further comprising sending a message, by the autosampler, to a solvent delivery system specifying an amount of time for completing the pre-injection operations.

5. The method of claim 4, further comprising receiving, by the autosampler, a reply to the message signifying that the solvent delivery system is in control of coordinating the solvent stream delivery with the pre-injection operations of the autosampler.

6. The method of claim 1, wherein
starting delivery of the solvent stream towards the autosampler occurs before the autosampler starts performing the pre-injection operations.

7. The method of claim 1, wherein starting delivery of the solvent stream occurs after the autosampler starts performing the pre-injection operations and before the autosampler completes performing the pre-injection operations.

8. A liquid chromatography system, comprising:
an autosampler performing pre-injection operations including making a sample ready for injection into a solvent stream, the autosampler configured to send a message specifying an amount of time for completing the pre-injection operations; and
a solvent delivery system in fluidic communication with the autosampler to deliver the solvent stream thereto and configured to receive the message sent by the autosampler and to determine a time difference between the amount of time for completing the pre-injection operations and an amount of time for delivering the solvent stream to the autosampler, the solvent delivery system starts delivery of the solvent stream towards the autosampler before the autosampler completes the pre-injection operations and the sample is ready for injection, wherein a first time at which delivery of the solvent stream starts and a second time at which the autosampler starts the pre-injection operations differ by approximately the time difference.

9. The liquid chromatography system of claim 8, further comprising receiving, by the autosampler, a reply to the message signifying that the solvent delivery system is taking control for coordinating delivery of the solvent stream with the pre-injection operations of the autosampler.

10. The liquid chromatography system of claim 8, wherein a buffer of time is added to the amount of time specified for completing the pre-injection operations.

11. The liquid chromatography system of claim 8, wherein the solvent delivery system triggers an injection event approximately at a time when the autosampler completes the pre-injection operations and the sample is ready for injection.

12. The liquid chromatography system of claim 8, wherein the solvent delivery system coordinates the start of the delivery of the solvent stream with when the autosampler starts the pre-injection operations such that the solvent stream arrives at the autosampler approximately at a time when the autosampler completes the pre-injection operations and the sample is ready for injection.

13. The liquid chromatography system of claim 8, wherein the solvent delivery system starts delivery of the solvent stream before the autosampler starts the pre-injection operations when the amount of time for delivering the solvent stream to the autosampler is greater than the amount of time for completing the pre-injection operations.

14. A method for introducing a sample into a solvent stream, comprising:
calculating a first amount of time for completing pre-injection operations of an autosampler and a second amount of time for delivering the solvent stream to the autosampler;
comparing the first amount of time and the second amount of time to identify which amount of time is greater than the other amount of time and to quantify a time difference between the amounts of time;
sending a first message from a solvent delivery system to the autosampler instructing the autosampler to initiate preparing the sample for injection into the solvent stream; and
sending, after a specified amount of time elapses after the first message is sent to the autosampler, a second message from the solvent delivery system to the autosampler to inject the sample into the solvent stream, wherein the specified amount of time is determined from the time difference.

15. The method of claim 14, further comprising receiving, by the solvent delivery system, a message that includes the specified amount of time needed by the autosampler to complete preparing the sample for injection into the solvent stream.

* * * * *

UNITED STATES PATENT AND TRADEMARK OFFICE
CERTIFICATE OF CORRECTION

PATENT NO. : 9,519,291 B2
APPLICATION NO. : 13/511667
DATED : December 13, 2016
INVENTOR(S) : John Heden et al.

Page 1 of 1

It is certified that error appears in the above-identified patent and that said Letters Patent is hereby corrected as shown below:

In the Specification

Column 4, Line 6:
• After "the ACQUITY" replace the letters "HPLC" with "UPLC"

Signed and Sealed this
Seventh Day of March, 2017

Michelle K. Lee
*Director of the United States Patent and Trademark Office*